(12) United States Patent
Eriksson et al.

(10) Patent No.: US 7,034,200 B2
(45) Date of Patent: Apr. 25, 2006

(54) NON-HUMAN TRANSGENIC ANIMALS EXPRESSING PLATELET-DERIVED GROWTH FACTOR C (PDGF-C) AND USES THEREOF

(75) Inventors: Ulf Eriksson, Stockholm (SE); Xuri Li, Stockholm (SE); Annica Ponten, Stockholm (SE); Karin Aase, Stockholm (SE); Hong Li, Stockholm (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/818,943

(22) Filed: Mar. 28, 2001

(65) Prior Publication Data

US 2002/0049987 A1    Apr. 25, 2002

Related U.S. Application Data

(60) Provisional application No. 60/192,507, filed on Mar. 28, 2000.

(51) Int. Cl.
   *G01N 33/00* (2006.01)
(52) U.S. Cl. .................. 800/3; 800/8; 800/18; 800/21; 800/24; 800/25; 435/7.21; 435/4; 435/354
(58) Field of Classification Search .................... 800/3, 800/8, 14, 23, 24, 25, 18, 21, 13; 435/325, 435/354, 7.21, 4
   See application file for complete search history.

(56) References Cited

U.S. PATENT DOCUMENTS 5,789,655 A * 8/1998 Prusiner et al. ................ 800/2
6,359,194 B1 * 3/2002 Galvin et al. ................ 800/18
6,432,673 B1 * 8/2002 Gao et al. ................... 435/69.1
6,492,575 B1 * 12/2002 Wagner et al. ................ 800/25

FOREIGN PATENT DOCUMENTS

WO    WO 99/47677    *  3/1999

OTHER PUBLICATIONS

Uutela et al., Chromosomal location, exon structure, and vascular expression patterns of the human PDGFC and PDGFD genes, 2001, CIRCULATION, vol. 103, pp. 2242-2247.*
Li et al., PDGF-C is a new protease-activated ligand for the PDGF alpha-receptor, 2000, Nature Cell Biology, vol. 2, pp. 302-309.*
Chiu et al., Optimizing energy potentials for success in protein tertiary structure prediction, 1998, Folding & Design, vol. 3, pp. 223-228.*
ACCESSION No. AF117608, Jan. 2, 2000.*
Polejaeva et al., New advances in somatic cell nuclear transfer: Application in transgenesis, 2000, THERIOGENOLOGY, vol. 53, pp. 117-126.*
Sigmund, Viewpoint: Are studies in genetically altered mice out of control, 2000, Thromb. Vasc. Biol., vol. 20, pp. 1425-1429.*
Rulicke et al., Germ line transformation of mammals by pronuclear microinjection, 2000, Experimental Physiology, vol. 85.6, pp. 589-601.*
Wall, Transgenic livestock: Progress and prospects for the future, THERIOGENOLOGY, vol. 45, pp. 57-68.*
Houdebine, Production of pharmaceutical proteins from transgenic animals, 1994, Journal of Biotechnology, vol. 34, pp. 269-287.*
Mullins et al., Perspective series: Molecular medicine in genetically engineered animals, 1996, J. Clin. Invest., vol. 97, pp. 1557-1560.*
Strojek et al., The use of transgenic animal techniques for livestock improvement, 1988, Genetic Engineering: Principles and methods, vol. 10, pp. 221-246.*
Humpherys et al., Epigenetic instability in ES cells and cloned mice, 2001, SCIENCE, vol. 293, pp. 95-97.*
Bishop, Chromosomal insertion of foreign DNA, 1996, Reprod. Nutr. Dev., vol. 36, pp. 607-618.*
Paigen et al., PubMed Accession No. 2317166, US National Library of Medicine, Bethesda, MD, Arteriosclerosis, Mar.-Apr. 1990, abstract, accessed by PTO on Jul. 21, 2003.*
Subranmaniam et al., The Journal of Biological Chemistry, 266: 24613-24620, 1991.*
Niemann, Transg. Res., 7:73-75, 1998.*
Philip M. Iannaccone, et al., Rapid Communication: Pluripotent Embryonic Stem Cells from the Rat Are Capable of Producing Chimeras. *Developmental Biology,* 163, 288-292 (1994).

* cited by examiner

*Primary Examiner*—Joseph Woitach
*Assistant Examiner*—Brian Whiteman
(74) *Attorney, Agent, or Firm*—Crowell & Moring LLP

(57) ABSTRACT

Non-human transgenic animals overexpressing PDGF-C and cells thereof have been created. The transgenic animals contain a nucleotide sequence that encodes for platelet derived growth factor C (PDGF-C) or an analog thereof, or a functional fragment of PDGF-C or analog thereof. These animals are useful for studying disease states characterized by overexpression of PDGF-C, as well as useful for evaluating therapies intended to treat such diseases.

17 Claims, 3 Drawing Sheets

10 mm

20 µm

NON-HUMAN TRANSGENIC ANIMALS EXPRESSING PLATELET-DERIVED GROWTH FACTOR C (PDGF-C) AND USES THEREOF

This application claims the priority of U.S. provisional application Ser. No. 60/192,507 filed Mar. 28, 2000 in the name of Ulf ERIKSSON et al.

This invention relates to non-human transgenic animals which overexpress PDGF-C and cells thereof that are useful for research on the effects that overexpression of PDGF-C has on an organism, and particularly for assaying substances which inhibit PDGF-C activity.

BACKGROUND OF THE INVENTION

Platelet-derived growth factors (PDGFs) are important in the growth, survival and function of connective tissue cells, fibroblasts, myofibroblasts and glial cells (Heldin et al., Growth Factor, 1993 8 245–252). In adults, PDGFs stimulate wound healing (Robson et al., Lancet, 1992 339 23–25). Structurally, PDGF isoforms are disulfide-bonded dimers of homologous A- and B-polypeptide chains, arranged as homodimers (PDGF-AA and PDGF-BB) or as a heterodimer (PDGF-AB).

PDGF isoforms exert their effects on target cells by binding to two structurally related receptor tyrosine kinases (RTKs). The alpha-receptor (PDGFR-alpha) binds both the A- and B-chains of PDGF, whereas the beta-receptor (PDGFR-beta) binds only the B-chain. These two receptors are expressed by many cell lines grown in vitro, and are mainly expressed in vivo by mesenchymal cells. The PDGFs exert their effects in vivo in a paracrine mode since they often are expressed in epithelial (PDGF-A) or endothelial (PDGF-B) cells in close apposition to the PDGFR-expressing mesenchyme. In tumor cells and in cell lines grown in vitro, coexpression of the PDGFs and the PDGFRs generates autocrine loops which are important for cellular transformation (Betsholtz et al., Cell, 1984 39 447–57; Keating et al., J. R. Coll Surg Edinb., 1990 35 172–4). Overexpression of the PDGFs has been observed in several pathological conditions, including malignancies, arteriosclerosis, and fibroproliferative diseases (reviewed in Heldin et al., The Molecular and Cellular Biology of Wound Repair, New York: Plenum Press, 1996, 249–273).

The importance of the PDGFs as regulators of cell proliferation and survival is well illustrated by recent gene targeting studies in mice that have shown distinct physiological roles for the PDGFs and their receptors despite the overlapping ligand specificities of the PDGFRs. Homozygous null mutations for either of the two PDGF ligands or the receptors are lethal. Approximately 50% of the homozygous PDGF-A deficient mice have an early lethal phenotype before embryonic day E10. The surviving animals have a complex postnatal phenotype with lung emphysema due to improper alveolar septum formation because of a lack of alveolar myofibroblasts (Boström et al., Cell, 1996 85 863–873). The PDGF-A deficient mice also have a dermal phenotype characterized by thin dermis, misshapen hair follicles and thin hair (Karlsson et al., Development, 1999 126 2611–2). PDGF-A is also required for normal development of oligodendrocytes and subsequent myelination of the central nervous system (Fruttiger et al., Development, 1999 126 457–67).

The phenotype of PDGFR-alpha deficient mice is more severe with incomplete cephalic closure, impaired neural crest development, cardiovascular defects, skeletal defects and edemas, leading to embryonic death around E8-16 (Soriano et al., Development, 1997 124 2691–70). The PDGF-B and PDGFR-beta deficient mice develop similar phenotypes that are characterized by renal, hematological and cardiovascular abnormalities and death at E17-19 (Levéen et al., Genes Dev., 1994 8 1875–1887; Soriano et al., Genes Dev., 1994 8 1888–96; Lindahl et al., Science, 1997 277 242–5; Lindahl, Development, 1998 125 3313–2). The renal and cardiovascular defects are due, at least in part, to the lack of proper recruitment of mural cells (vascular smooth muscle cells, pericytes or mesangial cells) to blood vessels (Levéen et al., Genes Dev., 1994 8 1875–1887; Lindahl et al., Science, 1997 277 242–5; Lindahl et al., Development, 1998 125 3313–2).

The PDGFs are members of the Platelet Derived Growth Factors/Vascular Endothelial Growth Factors (PDGF/VEGF) family of growth factors which presently consists of nine different members. The members of the PDGF/VEGF family are all characterized by the presence of eight conserved cysteine residues. In their active, physiological state, these proteins are dimers formed by disulfide bonding, by both inter- and intramolecular bonds, at the eight cysteine residues.

Besides PDGF-A and PDGF-B, the members of this family include VEGF and five proteins that are closely related to VEGF, and a new factor related to the PDGFs, designated PDGF-C. The five proteins closely related to VEGF are: VEGF-B, described in International Patent Application PCT/US96/02957 (WO 96/26736) which corresponds to U.S. Pat. No. 5,928,939 and in U.S. Pat. Nos. 5,840,693 and 5,607,918 by Ludwig Institute for Cancer Research and The University of Helsinki; VEGF-C or VEGF2, described in Joukov et al., EMBO J., 1996 15 290–298 and Lee et al., Proc. Natl. Acad. Sci. USA, 1996 93 1988–1992, and U.S. Pat. Nos. 5,932,540, 5,935,540 and 6,040,157 by Human Genome Sciences, Inc; VEGF-D, described in International Patent Application No. PCT/US97/14696 (WO 98/07832), and Achen et al., Proc. Natl. Acad. Sci. USA, 1998 95 548–553; the placenta growth factor (PlGF), described in Maglione et al., Proc. Natl. Acad. Sci. USA, 1991 88 9267–9271; and VEGF3, described in International Patent Application No. PCT/US95/07283 (WO 96/39421) by Human Genome Sciences, Inc. Each VEGF family member has between 30% and 45% amino acid sequence identity with VEGF. Functional characteristics of the VEGF and the VEGF-related proteins include varying degrees of mitogenicity for endothelial cells, induction of vascular permeability and angiogenic and lymphangiogenic properties.

Similarity between two proteins is determined by comparing the amino acid sequence and conserved amino acid substitutions of one of the proteins to the sequence of the second protein, whereas identity is determined without including the conserved amino acid substitutions.

VEGF is a homodimeric glycoprotein that has been isolated from several sources. Alterative mRNA splicing of a single VEGF gene gives rise to five isoforms of VEGF. VEGF shows highly specific mitogenic activity for endothelial cells. VEGF has important regulatory functions in the formation of new blood vessels during embryonic vasculogenesis and in angiogenesis during adult life (Carmeliet et al., Nature, 1996 380 435–439; Ferrara et al., Nature, 1996 380 439–442; reviewed in Ferrara and Davis-Smyth, Endocrine Rev., 1997 18 4–25). The significance of the role played by VEGF has been demonstrated in studies showing that inactivation of a single VEGF allele results in embryonic lethality due to failed development of the vasculature (Carmeliet et al., Nature, 1996 380 435–439; Ferrara et al., Nature, 1996 380 439–442). The isolation and properties of VEGF have been reviewed; see Ferrara et al., J. Cellular Biochem., 1991 47 211–218 and Connolly, J. Cellular Biochem., 1991 47 219–223.

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF is also chemotactic for certain hematopoetic cells. Recent literature indicates that VEGF blocks maturation of dendritic cells and thereby reduces the effectiveness of the immune response to tumors (many tumors secrete VEGF) (Gabrilovich et al., Blood, 1998 92 4150–4166 and Gabrilovich et al., Clinical Cancer Research, 1999 5 2963–2970).

VEGF-B has similar angiogenic and other properties to those of VEGF, but differs from VEGF in its distribution and expression in tissues. In particular, VEGF-B is very strongly expressed in heart and weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular retinoid acid-binding protein type I (CRABP-I). Its isolation and characteristics are described in detail in PCT/US96/02957 (WO 96/26736), in U.S. Pat. Nos. 5,840,693 and 5,607,918 by Ludwig Institute for Cancer Research and The University of Helsinki and in Olofsson et al., Proc. Natl. Acad. Sci. USA, 1996 93 2576–2581.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 1996 15 290–298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 1998 95 548–553). Its isolation and characteristics are described in detail in International Patent Application No. PCT/US97/14696 (WO98/07832).

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 1991 88 9267–9271. Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

As with the PDGFs, the VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

Most recently, an additional member of the PDGF/VEGF family of growth factors was identified, which is called PDGF-C. PDGF-C is described in International Patent Application PCT/US99/22668, filed Sep. 30, 1999, in U.S. application Ser. No. 09/410,349, filed Sep. 30, 1999, now abandoned, as well as in U.S. Provisional Application Ser. No. 60/192,507, filed Mar. 28, 2000, now abandoned. All three applications are specifically incorporated herein by reference.

PDGF-C has a two-domain structure not previously recognized within this family of growth factors, an N-terminal C1r/C1s/embryonic sea urchin protein Uegf/bone morphogenetic protein 1 (CUB) domain, and a C-terminal PDGF/VEGF homology domain (P/VHD). The structure of the P/VHD in PDGF-C shows a low overall sequence identity with other PDGF/VEGF homology domains, although the eight invariant cysteine residues involved in inter- and intra-molecular disulfide bond formation are present. The cysteine spacing in the central, most conserved region of this domain is different from other PDGF/VEGF domains, with an insertion of three amino acid residues. Despite the fact that the insertion occurs close to the loop 2 region which has been proposed to be involved in receptor binding, it was shown that this domain of PDGF-CC dimers binds PDGFR-alpha with an affinity almost identical to homodimers of PDGF-A or -B chains. In addition, four extra cysteine residues are present in this domain. Full length and truncated PDGF-CC dimers were found not to bind to VEGFR-1, -2 or -3, or to PDGFR-beta.

PDGF-C requires proteolytic removal of the N-terminal CUB domain for receptor binding and activation of the receptor. This indicates that the CUB domains are likely to sterically block the receptor binding epitopes of the unprocessed dimer. The in vitro and in vivo proteolytically processed proteins are devoid of N-terminal portions corresponding to more than 14–16 kDa as determined from SDS-PAGE analysis that is consistent with a loss of the 110 amino acid long CUB domain and a variable length portion of the hinge region between the CUB and core domains.

PDGF-C is not proteolytically processed during secretion in transfected COS cells indicating that proteolytic removal of the CUB domain occurs extracellularly, and not during secretion. This is in contrast to PDGF-A and -B (Östman et al., J. Cell. Biol., 1992 118 509–519) which appear to be processed intracellularly by furin-like endoproteases (Nakayama et al., Biochem J., 1997 327 625–635).

In situ localization studies demonstrate expression of PDGF-C in certain epithelial structures, and PDGFR-alpha in adjacent mesenchyme, indicating the potential of paracrine signaling in the developing embryo. PDGF-C expression seems particularly abundant at sites of ongoing ductal morphogenesis, indicating a role of the factor in connective tissue remodeling at these sites. The expression pattern is distinct from that of PDGF-A or PDGF-B indicating that the three growth factors have different roles despite their similar PDGFR-alpha binding and signaling activities. This is illustrated by the mouse embryonic kidney, in which PDGF-C is expressed in early aggregates of metanephric mesenchyme undergoing epithelial conversion, whereas PDGF-A is expressed in more mature tubular structures, and PDGF-B by vascular endothelial cells. PDGFR-alpha is expressed in the mesenchyme of the kidney cortex, adjacent to the sites of PDGF-C expression, indicating that this mesenchyme may be targeted specifically by PDGF-C. Indeed, PDGFR-alpha –/– mouse embryos show an extensive loss of the cortical mesenchyme adjacent to sites of PDGF-C expression, not seen in PDGF-A –/– mice or in PDGF-A/B –/– mice, indicating that PDGF-C has an essential role in the development of kidney mesenchyme.

Northern blots show PDGF-C mRNA in a variety of human tissues, including heart, liver, kidney, pancreas and ovary.

Transgenic manipulation can result in overexpression of a protein, making transgenic animal models useful tools to study the functions and physiological activities of proteins. A variety of such animal models have been produced for this purpose. One technique for producing transgenic animals involves the process of microinjection of a foreign DNA or transgene into the pronuclei of a fertilized egg. The introduced DNA appears to integrate randomly into the chromosome. Another technique for producing transgenic animals involves modifying an embryonic stem cell to overexpress a transgene.

SUMMARY OF THE INVENTION

In one of its aspects, the invention involves overexpression of PDGF-C or an analog thereof, or a functional activated fragment of PDGF-C or an analog thereof in non-human transgenic animals. In particular, the transgenic animals of the invention are useful in both understanding the effects of overexpressing PDGF-C and as a research tool for developing compounds that will inhibit the effects caused by overexpression of PDGF-C, such as development of hypertrophy and fibrosis in various organs, such as the heart.

The term "analog" or "functional analog" refers to a modified form of PDGF-C in which at least one amino acid substitution has been made such that the analog or functional analog retains substantially the same biological activity as the unmodified PDGF-C in vivo and/or in vitro.

There are many "biological activities of PDGF-C" that can be readily tested by methods known in the art, For example, the polypeptide or the encoded polypeptide from a polynucleotide has the ability to stimulate one or more of proliferation, differentiation, motility, survival or vascular permeability of cells expressing a PDGF-C receptor including, but not limited to, vascular endothelial cells, lymphatic endothelial cells, connective tissue cells (such as fibroblasts), myofibroblasts and glial cells. Preferably the polypeptide or the encoded polypeptide from a polynucleotide has the ability to stimulate wound healing. PDGF-C can also have antagonistic effects on cells.

As used herein, the term "PDGF-C" collectively refers to the polypeptides of SEQ ID NO:1 or SEQ ID NO:2, and fragments or analogs thereof which have the biological activities of PDGF-C as defined above, and to a polynucleotide which encodes PDGF-C, or a fragment or analog thereof having the biological activities of PDGF-C.

In another aspect, the invention provides a method for producing a transgenic, non-human animal overexpressing PDGF-C or an analog thereof, or a functional activated fragment of PDGF-C or an analog thereof. One method comprises introducing a transgenic DNA into the pronuclei of a fertilized egg of a non-human animal. The transgenic DNA is operably linked to a promoter. The egg is then implanted into a pseudopregnant non-human animal and allowed to develop into a transgenic animal. Examples of promoters that can be used include, but are not limited to, the alpha-myosin heavy chain promoter which gives cardiac myocyte-specific expression, the keratin K14 promoter which gives basal keratinocyte-specific expression and the insulin promoter which gives pancreatic beta cell-specific expression.

An alternative method of producing such a transgenic non-human animal is to modify an embryonic stem cell to overexpress PDGF-C or an analog thereof, or a functional activated fragment of PDGF-C or an analog thereof. This method comprises introducing a transgenic DNA into embryonic stem cells of a non-human animal. This cell is introduced into an animal embryo at a stage when the cell is capable of integrating, for example, at the blastocyte stage. The embryo is allowed to develop into a transgenic animal.

Subsequent to the production of a first generation of transgenic animals, a further alternative method is to mate a transgenic animal containing the sequences described here or made available by this invention with a second animal.

For example, a transgenic mouse according to the present invention can be mated with a wild-type mouse to produce 50% wild type and 50% heterozygous transgenic mice. The heterozygous transgenic mice offspring overexpress PDGF-C to the same degree as the parental generation.

Further, a transgenic mouse according to the present invention can be mated with a mouse transgenic for a trait other than PDGF-C overexpression. For example, the tsT A58 transgenic mouse (Immortomouse) that expresses the SV40 T antigen could be used, see Jat et. al., PNAS Vol. 88 pages 5096–5100 (1991). Cell lines isolated from a resultant mouse would be conditionally immortal. These cell lines would multiply when grown at 33° C. If the temperature was raised to 39° C., the cells would differentiate, allowing growth of cell lines such as cardiac myocyes. Cell lines could be isolated for the purpose of use in an assay on antagonists/agonists on PDGF-C.

The transgenic DNA used in any embodiment of the method of the invention comprises a sequence of polynucleotides coding for PDGF-C or an analog thereof, or a functional activated fragment of PDGF-C or an analog thereof. The polynucleotides coding for PDGF-C or an analog thereof, or a functional activated fragment of PDGF-C or an analog thereof may have been modified in a number of ways known in the art but still retain all or part of the biological activity of PDGF-C.

The "modified polynucleotides coding for PDGF-C" of this invention refers to a sequence of polynucleotides coding for PDGF-C or an analog thereof, or a functional activated fragment of PDGF-C or an analog thereof that has been modified by an in vitro or recombinant DNA technique. Modifications including deletions, substitutions, and insertions of nucleotides into the polynucleotide sequence are specifically included.

Preferably where amino acid substitution is used, the substitution is conservative, i.e. an amino acid is replaced by one of similar size and with similar charge properties.

Conservative substitution denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. Conservative substitution also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

Conservative Substitutions I

| SIDE CHAIN CHARACTERISTIC | AMINO ACID |
|---|---|
| Aliphatic | |
| Non-polar | G A P |
|  | I L V |
| Polar - uncharged | C S T M |
|  | N Q |
| Polar - charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:N.Y. (1975), pp. 71–77] as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |

TABLE C-continued

Conservative Substitutions III

| Original Residue | Exemplary Substitution |
|---|---|
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

In yet another aspect, the invention provides a method for screening compounds for the ability to inhibit the effects of PDGF-C, such as hypertropy or fibrosis of the heart, liver, kidney, pancreas, ovaries, and other tissues. The method comprises introducing the compound into a transgenic animal comprising cells which overexpress PDGF-C and monitoring, by any suitable means, an inhibition in the biological activity of PDGF-C in the animal. Monitoring includes but is not limited to comparing the wildtype and transgenic animals.

BRIEF DESCRIPTION OF THE DRAWINGS

The invention will be described in further detail hereinafter with reference to the accompanying drawings in which.

DETAILED DESCRIPTION OF ILLUSTRATIVE EMBODIMENTS

Figure 1:
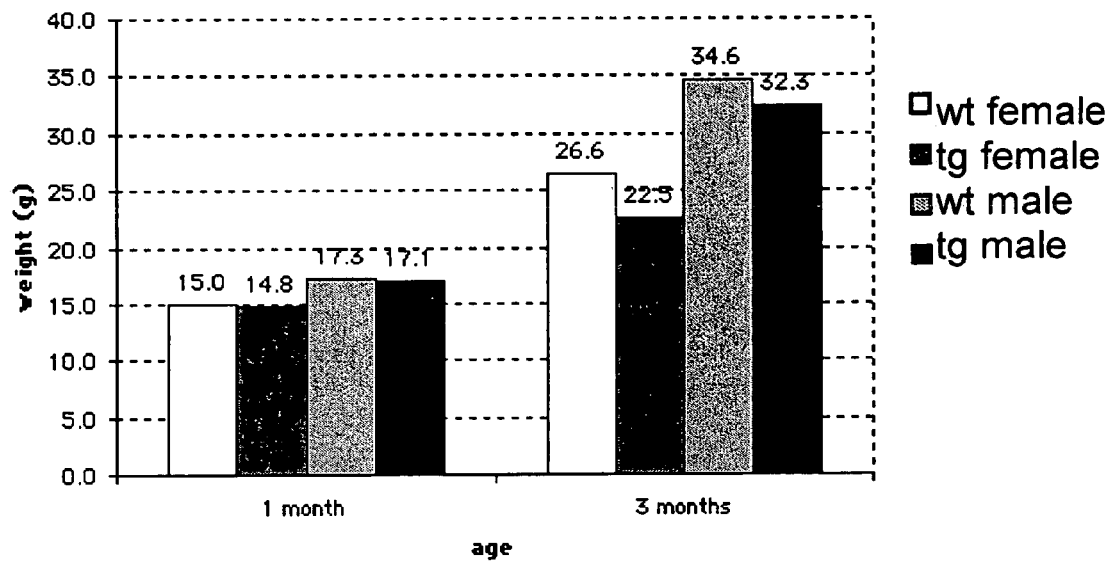
FIG. 1 shows body weights of normal (wild type, wt) and transgenic (tg) mice at one and three months of age.

The descriptions and examples below are exemplary of the embodiments and scope of this invention. The invention is not limited to the scope of this description.

Persons skilled in the art will appreciate that the following examples and embodiments may be modified using techniques known in the art. For example, variations in the nucleic acid sequences described or claimed can be produced by known methods without altering the effects or advantages the inventors have shown. Such variations are therefore included within the scope of this description and invention.

In addition, detailed protocols for many of the techniques known in the art are described by Ausubel, F. M. et al. Eds. *Current Protocols in Molecular Biology*, Greene Publishing Associates and Wiley-Interscience, John Wiley & Sons, Boston, Mass. (1989), and Supplements through January 1997; in Sambrook, J., et al., *Molecular Cloning. A Laboratory Manual*, 2nd Ed., Cold Spring Harbor Laboratory Press, Cold Spring Harbor, N.Y. (1989); in B. Hogan et al. Eds. *Manipulating the Mouse Embryo. A Laboratory Manual*, Cold Spring Harbor Laboratory Press, (1994); and in Gordon and Ruddle, Science, 1981 214 1244–1246. These documents are specifically incorporated herein by reference, and may be relied on to evidence enablement of one skilled in the art to practice the embodiments of the invention.

Transgenic DNA refers to DNA that is introduced into a cell so that the DNA is incorporated into the genome of the cell. The cell may be capable of giving rise to a transgenic animal which contains the transgenic DNA. Generally, the transgenic DNA for administration into a particular cell can be constructed using a transgenic vector. A preferred DNA is a polynucleotide that encodes for full-length PDGF-C or an analog thereof, and a more preferred DNA is that which encodes for the activated truncated PDGF-C or an analog thereof. The truncated portion of PDGF-C comprises at least a portion of the PDGF/VEGF homology domain (P/VHD) of PDGF-C. The minimal sequence is residues 230–345 of SEQ ID NO:1. However, the domain can extend towards the N terminus up to residue 164 of SEQ ID NO:1. Herein the P/VDH of PDGF-C is defined as truncated PDGF-C. The truncated PDGF-C is an activated form of PDGF-C.

A recombinant gene or sequence simply means the gene or sequence has been manipulated in any one of a number of recombinant DNA techniques known in the art.

As used herein the term "modified polynucleotide sequence coding for PDGF-C" refers to a PDGF-C polynucleotide sequence from an animal which has been modified by one or more of: point mutations, site-directed mutagenesis, deletions, and insertions. Alternatively, a modified polynucleotide sequence coding for PDGF-C is a sequence which is linked to a second sequence, such as a marker sequence, epitope tag or promoter/enhancer, which is not associated with wild type PDGF-C DNA. PDGF-C encoded by a modified polynucleotide sequence retains some or all of the activities of wild type PDGF-C, for example, the PDGFR-alpha binding motif.

The FLAG™ peptide can be used as an epitope tag in may cell types. The sequence, use and detection of the FLAG™ tag is described in Chubet, RG, et. al., Vectors for expression and secretion of FLAG epitope-tagged proteins in mammalian cells, *Biotechniques* 1996 January; 20(1):136–41. Constructing a mammalian expression vector using, for example GAL4 and a Flag peptide is described in Witzgall, R., et. al., A mammalian expression vector for the expression of GAL fusion proteins with an epitope tag and histidine tail, *Anal Biochem* 1994 December; 223(2):291–8.

As noted above, there are many known processes for generating transgenic animals. These processes are essentially the same regardless of the species involved. While the Examples that follow describe transgenic mice, the same techniques may be used to produce non-mouse transgenic animals, and their creation and use is encompassed within the scope of this invention.

One process begins with transgenic DNA operably linked to a promoter. The transgenic DNA-promoter complex is introduced into the pronuclei of a fertilized egg of a non-human animal. The egg is then implanted into a pseudopregnant non-human animal and allowed to develop into a transgenic animal.

Fertilized eggs from a variety of animals used in the above described method can be produced using techniques well known to those of ordinary skill in the art. For example, the use of bovine oocytes to support embryos of a number of species is described in Dominko, T., et. Al., Bovine oocyte cytoplasm supports development of embryos produced by nuclear transfer of somatic cell nuclei from various mammalian species, *Biol Reprod*, 1999 June; 60(6):1496–502.

Alternatively, fertilized eggs from a variety of animals can be obtained from a number of sources. These various species include mice, cows, rabbits, and sheep, as well as other animals (Mullins et al, J. Clin. Invest., 1996 98 S37–S40). Accordingly, the invention is as applicable to animals other than the specifically exemplified mice. While many of the references regarding the state of the art relate to mammalian species, the invention is applicable and enabled to animals other than mammals.

A second method for producing transgenic animals involves the modification of embryonic stem (ES) cells. This second method comprises introducing transfected cells into embryos at a stage at which they are capable of integrating into the embryo, for example, at the blastocyte stage. The embryo with transfected cells is then replanted into a surrogate mother, resulting in chimeric offspring possessing the transgenic DNA.

Embryonic stem cells are available from a number of sources. These include mice, rats, cows, pigs, sheep, and other animals (Joyner A. L., (1993), *Gene Targeting*). Alternatively, the production of ES cells from a variety of animals is well known to those of ordinary skill in the art. *A practical approach*, edited by Wood, R. and Hames, B. D., The Practical Approach Series, vol. 126, Oxford IRL Press (specifically incorporated herein by reference) describes methods of producing ES cells. Also, B. Hogan et al., Eds., *Manipulating the Mouse Embryo. A laboratory Manual*, Cold Spring Harbor Laboratory Press, (1994) describes manipulating the mouse embryo.

Methods used in successful research with rat ES cells are described in Iannaccone, PM, et. al., Pluripotent embryonic stem cells from the rat are capable of producing chimeras, *Dev Biol*, 1994 May; 163(1):288–92. Work with rabbit ES cells is described in Schoonjans, L., et. al., Pluripotential rabbit embryonic stem (ES) cells are capable of forming overt coat color chimeras following injection into blastocysts, *Mol Reprod Dev*, 1996 December; 45(4):439–43. In addition, Couly and Le Douarin, Development, 1990 108 543–555, describes methods for isolating and manipulating chicken and quail embryos. Kimmel and Warga, Nature, 1987 327 234–237, describe isolation and manipulation of zebrafish embryos. Ware et al., "Development of Embryonic Stem Cell Lines from Farm Animals," Society for the Study of Reproduction, 1988 38 241 also discusses an embryonic stem cell culture condition amenable for many species like mouse, cattle, pig, and sheep.

Specific references for pig embryonic stem cells include Notarianni E., et. al., Incorporation of cultured embryonic cells into transgenic and chimeric, porcine fetuses, *Int J Dev Biol*, 1997 June; 41(3):537–40 and Gutierrez-Adan, et. al., Isolation of Pluripotent Stem Cells from Cultured Porcine Primordial Germ Cells, *Biol Reprod*, November; 57(5) : 1089–95 (1997). Specific references for cows are Cibelli, et. al., Transgenic Bovine Chimeric Offspring Produced from Somatic Cell-Derived Stem-Like Cells, *Nat. Biotechnol*, July; 16(7) :642–6 (1998) and Kubota C., et. al., Six cloned calves produced from adult fibroblast cells after long-term culture, *Proc Natl Acad Sci USA,* 2000 February 1; 97(3): 990–5. Preparing primate embryonic stem cells can be facilitated by referring to Thompson, et. al., Isolation of a Primate Embryonic Stem Cell Line, *Proc. Natl Acad Sci USA*, August 15; 92(17):7844–8 (1995).

Various methods are known in the art for introducing DNA into animal cells, for example, ES cells. Transgenic DNA can be microinjected into the appropriate cells. Also, viral vectors can be used to introduce the DNA into appropriate cells and the genome of those cells (See, for example, Tsukui et al., Nature Biotechnology, 1996 14 982–985). Or, cells can be manipulated in vitro through transfection and electroporation methods (See, for example, Ausubel, F. M. et al. Eds. *Current Protocols in Molecular Biology*, Greene Publishing Associates and Wiley-Interscience, John Wiley & Sons, Boston, Mass. (1989); and B. Hogan et al., Eds., *Manipulating the Mouse Embryo. A Laboratory Manual*, Cold Spring Harbor Laboratory Press, (1994)).

Generally, this type of transgenic DNA incorporates into a cell genome through random integration, although homologous recombination is possible. The design of transgenic DNA vectors involves linking the transgenic DNA to an appropriate promoter sequence. Examples of promoters that can be used include, but are not limited to, alpha-myosin heavy chain promoter which gives cardiac myocyte-specific expression, keratin K14 promoter which gives basal keratinocyte-specific expression, and insulin promoter which gives pancreatic beta cell-specific expression.

EXAMPLES

Mice overexpressing PDGF-C were created to analyze the role of PDGF-C in development and maintenance in vivo under diseased states. The transgenic mice were constructed to overexpress a c-myc epitope-tagged PDGF-C using the alpha-myosin heavy chain (alpha-MHC) promoter (Subramaniam, A. et al., J. Biol. Chem. 1991 266 24613–24620).

Example 1

Insertion of the Transgenic Vector into an Animal Cell

The sequence encoding the human c-myc epitope (Evan, G. I. et al., Mol. Cell Biol., 1985 5 3610–3616) was introduced at the 3' end of the coding region of mouse PDGF-C cDNA by PCR mutagenesis with DeepVent polymerase (Biolabs). The primers used for PCR were 5'-CG-GAATTCTCAGCCAAATGCTCCTCCTC (forward) (SEQ ID NO:3) and 5'-CGGATTTCTTACAAGTCTTCTTCA-GAAATAAGCTTTTGTTCCCCTCCTGCGTTTCCTCT (reverse) (SEQ ID NO:4). This generated a 1100 bp fragment which was subcloned into the pBluescript-based transgenic vector between the 5.5 kb mouse alpha-myosin heavy chain promoter and the 250 bp polyadenylation sequence from SV-40 (Subramaniam, A., et al., J. Biol. Chem. 1991 266 24613–24620). The linearized and purified transgene fragment was microinjected into the male pronuclei of fertilized mouse oocytes (Mouse Camp, Karolinska Institutet, Stockholm).

Example 2

Production of Transgenic Animals

The injected fertilized oocytes were implanted into pseudopregnant foster mothers. Tail DNA was collected from the resulting heterozygous pups. Generally, 0.5 cm of tail tissue was surgically removed and used to prepare DNA samples. The tail DNA was screened for the presence of the transgene by PCR using the mouse PDGF-C specific primer, 5'-GTGTCCATACGGGAAGAG (forward) (SEQ ID NO:5) and the human c-myc specific primer 5'-GTCTTCTTCA-GAAATAAGC (reverse) (SEQ ID NO:6). A 294 bp fragment was amplified in the transgenic founders. Male founders were backcrossed to C57Bl/6 wildtype females.

Example 3

Comparative Body and Heart Weights at One and Three Months of Age

Body and heart weights were measured at one and three months of age for both normal (wild type, wt) and transgenic (tg) mice. Live mice were weighed on a normal laboratory scale and heart weights were obtained after dissection of the hearts.

Figure 2:
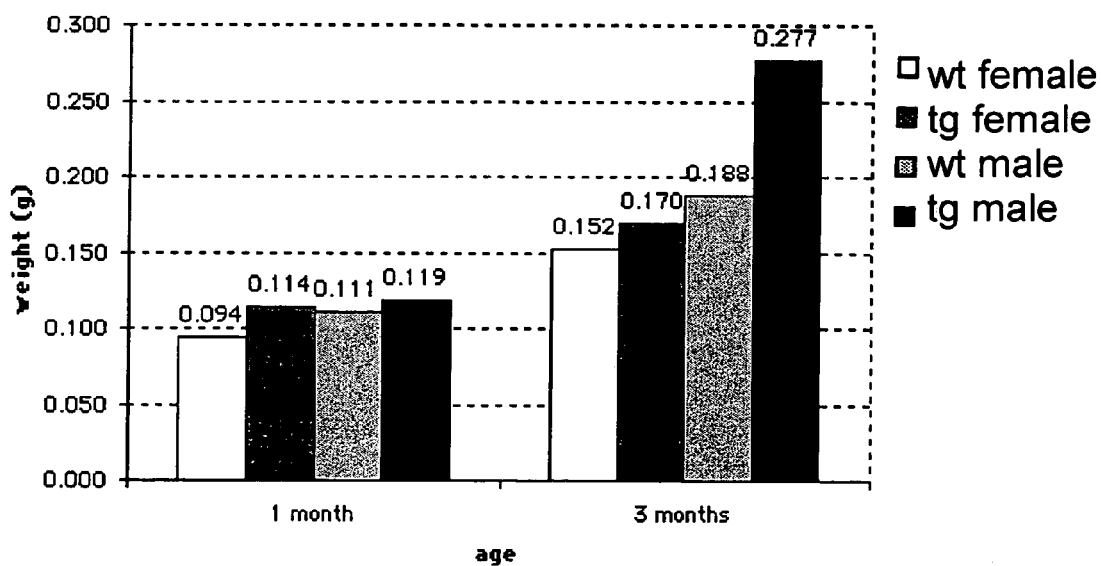
FIG. 2 shows heart weights of normal and transgenic mice at one and three months of age.

The weights were sorted by type (normal or transgenic), sex (male or female) and age (one or three months) . The data for body weight are summarized in FIG. 1. A general reduction in body weight is seen in the transgenic animals. The data for heart weight are summarized in FIG. 2. Heart weights increase in the transgenic animals, particularly in the male mice.

Example 4

Comparative Heart Studies at Six to Eight Weeks of Age

At six to eight weeks of age, transgenic and normal animals were killed and their hearts removed, washed in ice cold PBS and prepared for routine histology and biochemical analysis. Hearts were fixed in 4% paraformaldehyde in PBS overnight at 4° C, dehydrated, embedded in paraffin wax and sectioned. The tissue sections were stained in hematoxylin/eosin using standard techniques.

Figure 3A:
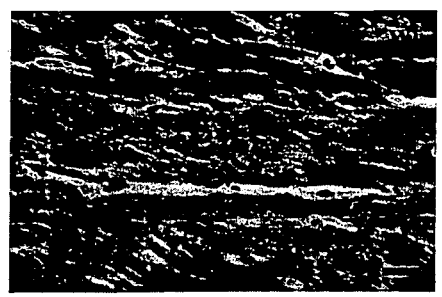
FIG. 3A shows a tissue section from a normal (wild type, wt) mouse heart.
Figure 3B:
FIG. 3B shows a tissue section from a transgenic (tg) mouse heart.

Analysis of tissue sections from hearts of adult normal (wild type, wt) (FIG. 3A) and transgenic (tg) animals (FIG. 3B) showed that overexpression of PDGF-C induced a strong proliferation of myocardial interstitial cells, e.g. cardiac fibroblasts. Cardiac fibroblasts express PDGFR-alpha and PDGF-AA dimer has previously been shown to be a potent mitogen for this cell type (Simm, A. et al., *Basic Res. Cardiol.* 1998 93 Suppl 3: 40–43). The expansion of the interstitium in the transgenic hearts caused a drastic disorganization of the cardiac myofibers indicating that the functional properties of the transgenic hearts were severely compromised.

For biochemical analysis, hearts were minced and then sonicated in ice cold 10 mM Tris-HCl buffer pH 7.6 containing 0.1M NaCl, 1 mM EDTA, 1 mg/ml aprotinin and 4 mM phenylmethylsulfonyl fluoride. Supernatants were collected after centrifugation at 12,000 g for 20 min at 4° C., and aliquots were subsequently subjected to SDS-PAGE under reducing conditions. For immunoblotting analysis anti-c-myc mouse ascites (9E10) and a rabbit anti-mouse PDGF-C peptide antiserum were used. The rabbit anti-mouse PDGF-C peptide antiserum was generated using the peptide CVKKSRVVNLNLLKEEVKLYSC (SEQ ID NO:7) (residues 230–250 of mouse PDGF-C (SEQ ID NO:2)) as described in International Application No. PCT/US99/22668. Bound antibodies were visualized using the ECL technique.

Figure 4:
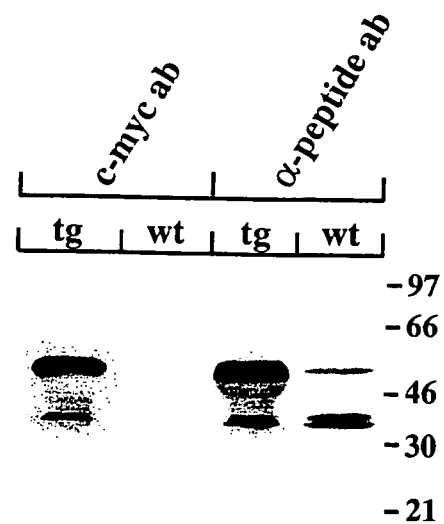
FIG. 4 shows the results of SDS-PAGE and immunoblotting of tissue extracts from transgenic (tg) and normal (wild type, wt) mouse hearts.

FIG. 4 shows the results of the analysis of SDS-PAGE and immunoblotting of tissue extracts from normal and transgenic mouse hearts. Transgenic c-myc epitope-tagged PDGF-C was visualized using a c-myc-specific monoclonal antibody (c-myc MAb). Analysis under reducing conditions showed abundant expression of full-length 52 kDa c-myc-tagged PDGF-C in transgenic hearts and the presence of several processed intermediates with a 34 kDa species being most prominent. Similar analysis using the anti-peptide antiserum to PDGF-C confirmed these results. The analysis indicates that proteases able to convert overexpressed latent full-length PDGF-C in vivo are expressed in the myocardium, and that activated PDGF-C is able to promote proliferation of PDGFR-alpha expressing cardiac fibroblasts.

The heart phenotype induced in the PDGF-C transgenic animals, with an expansion of the cardiac interstitium, is reminiscent of myocardial hypertrophy and fibrosis. Cardiac fibroblasts synthesize the extracellular matrix and play a pivotal role in adaptation and remodelling of the interstitium, typically seen following myocardial infarctions and increased hemodynamic load. Given that PDGF-C is normally expressed in heart, this indicates that PDGF-C has a role in physiological and pathophysiological remodelling of the cardiac interstitium.

As cardiac fibrosis is a common consequence following heart infarction, an animal model can be used both to understand the mechanisms underlying this phenomena and as a research tool for developing drugs that may interfere with development of hypertrophy and cardiac fibrosis.

Example 5

Comparative Heart Gross Examinations at Six Months of Age

Figure 5:
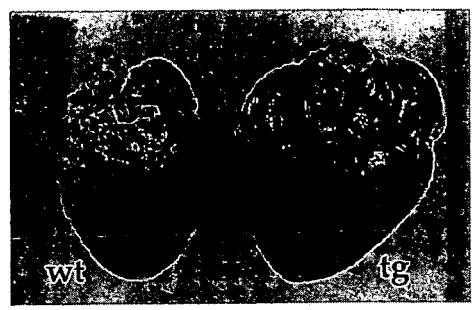
FIG. 5 shows a normal (wild type, wt, to the left) and a transgenic (tg, to the right) mouse heart from 6 month old male mice.

Hearts were obtained from normal and transgenic male mice at age six months. FIG. 5 shows a normal (wild type, wt) heart on the left and a transgenic (tg) heart on the right. There is an observable general increase in size of the transgenic mouse heart, with a prominent enlargement of the atrial region.

Example 6

Comparative Heart Histological Evaluations at Six Months of Age

Hearts were collected from six month old mice. The hearts were prepared in paraffin-embedded fixed tissue blocks and regular (5 μm) sections were taken. The sections were rehydrated and treated with trypsin (1×TRYPSIN-EDTA, LIFE TECHNOLOGIES) for 20 minutes at 37° C. The sections were then stained for PECAM-1 expression, and endothelial cell marker, using TSA™-Indirect as suggested by the supplier (NEN™ Life Science Products). The primary antibody, rat α PECAM-1 antibody (Pharmingen), was incubated at a dilution of 1:500 and the secondary antibody, biotinylated rat α IgG (mouse adsorbed, Vector Laboratories), was incubated at a dilution of 1:300. The chromogenic substrate used was 3,3'-DAB (Sigma).

Figure 6A:
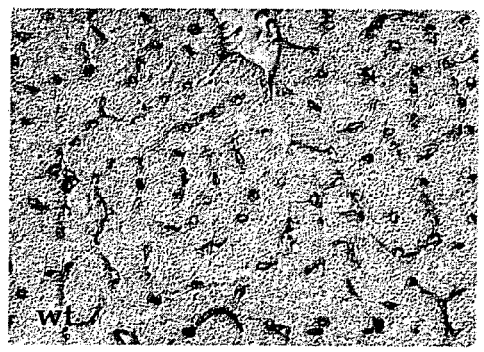
FIG. 6A shows microvessel organization in a stained heart left ventricle section from a normal (wild type, wt) six month old mouse.
Figure 6B:
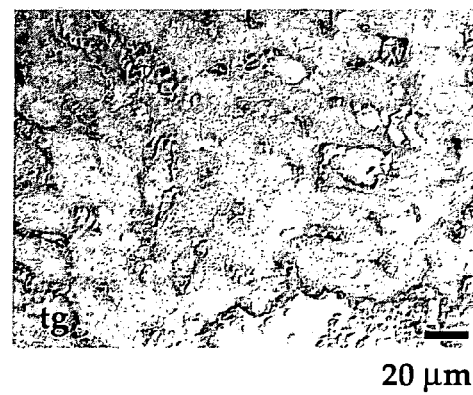
FIG. 6B shows microvessel disorganization in a stained heart left ventricle section from a transgenic (tg) six month old mouse.

Photographs of the left ventricles were taken and are reproduced in FIGS. 6A and 6B. It can be observed that microvessel organization in the wild-type (wt, FIG. 6A) mouse heart shows an even distribution of capillaries. In contrast, the disorganized microvessels evident in the transgenic mouse heart (FIG. 6B) show a loss of capillaries and the formation of unevenly distributed vascular sac-like structures. The formation of these sac-like structures is likely a sign of proliferation of the vasculature. Sac-like structure formation may be an indirect sign of unsufficient vascular supply to the heart. This type of microvessel disease is frequently observed in human disease, particularly in heart fibrosis.

Example 7

Comparative Heart Histological Evaluations

Further analysis was conducted by staining wild type and transgenic hearts with Mason trichromate to show deposition of extracellular matrix. Regular sections from paraformaldehyde-fixed and paraffin-embedded tissue blocks were deparaffinized and hydrated with 2×xylene for 5 minutes, 2×abs for 3 minutes, 2×95% for 3 minutes, 70% for 5 minutes, followed by $dH_2O$. Bouin's solution (a mixture of 75 ml saturated aqueous picric acid, 25 ml of concentrated (37–40%) formalin, and 5 ml of glacial acetic acid) was preheated to 58° C and the sections were incubated in the solution for 15 minutes. The sections were washed in running water approximately 4–10 minutes, until the yellow color disappeared, then rinsed twice with $dH_2O$.

A working solution of Modified Weighert's iron hematoxylin was prepared using equal parts of solution A and solution B and stored protected from light. Solution A consists of 2 grams of hematoxylin crystals (C.I. 75290) and 100 ml of 90% alcohol. Solution B consists of 4 ml of 62% aqueous ferric chloride ($FeCl_3$ 6Hx), 95 ml of $dH_2O$, and 1 ml of concentrated HCl.

After the proceeding steps, the sections were placed in the Modified Weigert's solution for 2 minutes, then washed in running water and rinsed twice with $dH_2O$. Next, Biebrich scarlet-acid fuchsin (90 ml of 1% aqueous Biebrich scarlet (C.I. 26905) with 10 ml of 1% aqueous acid fuchsin (C.I. 42685) and 1 ml glacial acetic acid, stored protected from light) was applied for a few seconds, followed by three rinses with $dH_2O$. The sections were placed in phosphomolybdic-phosphotungstic acid solution (2.5 g of phosphomolybdic acid, 2.5 g of phosphotungstic acid, and 100 ml $dH_2O$) for 5 minutes, followed by 30 minutes in water blue solution (3 g of water blue, 2 ml of glacial acetic acid, and 100 ml $dH_2O$, stored protected from light). The sections were carefully rinsed with $dH_2O$. Acetic acid solution (1 ml glacial acetic acid with 100 ml $dH_2O$) was applied for 3 minutes, followed by two rinses with $dH_2O$.

The sections were then dehydrated in alcohol series to histoclear and mounted with entellan. The sections were allowed to dry in a hood. The staining yielded black nuclei, blue collagen, and red cytoplasm, keratin, muscle fibers, and fibrin.

This procedure revealed staining in hearts from one month old transgenic animals similar to staining in the hearts of wild type animals. However, the phenotype gets progressively worse with age. At three months of age, hearts from transgenic animals show significant deposition of the extracellular matrix. At six months of age, hearts from transgenic animals show extensive deposition of the extracellular matrix.

This example demonstrates PDGF-C overexpression in transgenic animals causes proliferation of cardiac fibroblasts and a resultant expansion of the interstitum. The overexpression of PDGF-C may also induce the fibroblasts to secrete more extracellular matrix, essentially collagens. This example provides further evidence that the overexpression of PDGF-C induces fibrosis.

Example 8

Method for PDGF-C Antagonist Compound Identification in an Animal System

A compound is identified as a PDGF-C antagonist by introducing the compound into a transgenic, non-human animal which overexpresses PDGF-C or an analog thereof, or a functional fragment of PDGF-C or an analog thereof. Following introduction of the compound, biological activity of PDGF-C in the animal is monitored. An inhibition of PDGF-C biological activity indicates the compound may be useful as a PDGF-C antagonist. Comparing biological activity of PDGF-C could involve comparing the transgenic animal with a normal (wild type) animal of the same species.

Example 9

Method for PDGF-C Antagonist Compound Identification in a Cellular System

A compound is identified as a PDGF-C antagonist by introducing the compound into a cell or cells isolated from a transgenic, non-human animal which overexpresses PDGF-C or an analog thereof, or a functional fragment of PDGF-C or an analog thereof. Following introduction of the compound, biological activity of PDGF-C in the cell or cells is monitored. An inhibition of PDGF-C biological activity indicates the compound may be useful as a PDGF-C antagonist.

Example 10

Method for Screening Compounds Targeted to Hypertrophy

A compound may be evaluated for its ability to inhibit hypertrophy by administering a pharmaceutically active amount of the compound to a transgenic, non-human animal which overexpresses PDGF-C or an analog thereof, or a functional fragment of PDGF-C or an analog thereof. Following introduction of the compound, the animal's cardiac development is monitored. Normal cardiac development in the animal may indicate the compound is useful in the inhibition of hypertrophy.

Example 11

Method for Screening Compounds Targeted to Fibrosis

A compound may be evaluated for its ability to inhibit fibrosis by administering a pharmaceutically active amount of the compound to a transgenic, non-human animal which overexpresses PDGF-C or an analog thereof, or a functional fragment of PDGF-C or an analog thereof. Following introduction of the compound, the animal's cardiac development is monitored. Normal cardiac development in the animal may indicate the compound is useful in the inhibition of fibrosis.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof. All references cited herein are expressly incorporated by reference.

What is claimed is:

1. A method for producing a transgenic mouse, the method comprising the steps of:
   a) introducing a polynucleotide into a mouse cell, wherein said polynucleotide is operably linked to a heart-specific promoter and encodes a polypeptide comprising SEQ ID NO:1 or SEQ ID NO:2;
   b) allowing said cell from step a) to develop into a transgenic mouse,
   wherein said cell of step a) is a pronuclei of a fertilized oocyte, said method further comprising implanting said fertilized oocyte into a pseudopregnant mouse; or
   wherein said cell of step a) is an embryonic stem cell; said polynucleotide is integrated into a genomic DNA of said embryonic stem cell; and said embryonic stem cell is introduced into a developing embryo, and
   wherein the transgenic mouse overexpresses the polypeptide comprising SEQ ID NO: 1 or SEQ ID NO: 2 and develops myocyte hypertrophy or heart fibrosis during its life time.

2. A method for producing a transgenic mouse, the method comprising the steps of:
   a) introducing a polynucleotide into a mouse cell, wherein said polynucleotide is operably linked to an alpha-myosin heavy chain promoter, and encodes a polypeptide comprising SEQ ID NO:1 or SEQ ID NO:2;
   b) allowing said cell from step a) to develop into a transgenic mouse,
   wherein said cell of step a) is a pronuclei of a fertilized oocyte, said method further comprising implanting said fertilized oocyte into a pseudopregnant mouse; or
   wherein said cell of step a) is an embryonic stem cell; said polynucleotide is integrated into a genomic DNA of said embryonic stem cell; and said embryonic stem cell is introduced into a developing embryo, and
   wherein the transgenic mouse overexpresses the polypeptide comprising SEQ ID NO: 1 or SEQ ID NO: 2 and develops myocyte hypertrophy or heart fibrosis during its life time.

3. The method of claim 1, wherein said polynucleotide is operably linked to an epitope tag.

4. The method of claim 3, wherein the epitope tag is c-myc.

5. The method of claim 1, wherein said polynucleotide is operably linked to a marker sequence.

6. The transgenic mouse produced by the method of claim 1, wherein said polynucleotide is stably integrated into the genome of the mouse and wherein the transgenic mouse develops myocyte hypertrophy or heart fibrosis during its life time.

7. A transgenic mouse that is a descendant from the mouse according to claim 6, wherein the transgenic mouse overexpresses the polypeptide comprising SEQ ID NO: 1 or SEQ ID NO: 2 and develops myocyte hypertrophy or heart fibrosis during its life time.

8. The mouse according to claim 6, wherein the mouse is homozygous with regard to the polynucleotide.

9. A cell isolated from the mouse according to claim 6.

10. A fertilized mouse oocyte containing a polynucleotide molecule that is operably linked to a heart-specific promoter and that encodes a polypeptide comprising the amino acid sequence of SEQ ID NO:1 or SEQ ID NO:2.

11. A transgenic mouse embryonic stem cell containing a polynucleotide molecule that encodes a polypeptide comprising the amino acid sequence of SEQ ID NO:1 or SEQ ID NO:2.

12. A method for identifying a compound as a PDGF-C antagonist, said method comprising:
   introducing a candidate compound into the transgenic mouse according to claim 6; and
   monitoring a biological activity of PDGF-C in said mouse;
   wherein inhibition of the PDGF-C biological activity indicates that the candidate compound is a PDGF-C antagonist.

13. A method for identifying a compound as a PDGF-C antagonist, said method comprising the steps of:
   exposing to said compound a test cell isolated from the transgenic mouse according to claim 6;
   assaying an effect of said compound on a PDGF-C activity of said test cell in vitro;

comparing PDGF-C activity in a cell isolated from the transgenic mouse not exposed to said compound, and identifying said compound as a PDGF-C antagonist where the PDGF-C biological activity of said test cell is altered as compared to the PDGF-C activity of the control cell.

14. A method of screening for a compound for inhibition of hypertrophy, comprising the steps of:
    administering a candidate compound to a test transgenic mouse according to claim 6;
    monitoring cardiac development of said test mouse;
    monitoring cardiac development of a control transgenic mouse according to claim 6 not exposed to said candidate compound; and
    wherein inhibition of cardiac development in said test mouse when compared to the control transgenic mouse in the absence of said candidate compound indicates that the candidate compound inhibits hypertrophy.

15. A method of screening for a compound for inhibition of fibrosis, comprising the steps of:
    administering a candidate compound to a test transgenic mouse according to claim 6; and
    monitoring cardiac development of said test mouse;
    monitoring cardiac development of a control mouse according to claim 6 not exposed to said candidate compound; and
    wherein inhibition of cardiac development in the test mouse when compared to the control transgenic mouse in the absence of said candidate compound indicates that the candidate compound inhibits fibrosis.

16. The transgenic mouse according to claim 6, wherein the mouse is heterozygous with regard to the polynucleotide encoding a polypeptide comprising the amino acid sequence SEQ ID NO:1 or SEQ ID NO:2.

17. A method for producing a transgenic mouse, the method comprising the steps of:
    a) introducing a polynucleotide into a mouse embryonic stem cell, said polynucleotide is operably linked to a heart-specific promoter, and encodes a polypeptide comprising the sequence of SEQ ID NO:1 or SEQ ID NO:2, and
    b) introducing said embryonic stem cell into a developing embryo which is allowed to develop into a transgenic mouse,
    wherein the transgenic mouse overexpresses the polypeptide comprising SEQ ID NO: 1 or SEQ ID NO: 2 and develops hypertrophy or fibrosis in its heart in its life time.

* * * * *

SEQUENCE LISTING

```
<160> NUMBER OF SEQ ID NOS: 7

<210> SEQ ID NO 1
<211> LENGTH: 345
<212> TYPE: PRT
<213> ORGANISM: Homo sapiens

<400> SEQUENCE: 1

Met Ser Leu Phe Gly Leu Leu Leu Val Thr Ser Ala Leu Ala Gly Gln
1               5                   10                  15

Arg Arg Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
```

```
              100                 105                 110
Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Val Leu
                165                 170                 175

Pro Pro Ser Ala Leu Pro Leu Asp Leu Asn Asn Ala Ile Thr Ala
            180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
            210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
            290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Cys Asp
                325                 330                 335

Cys Val Cys Arg Gly Ser Thr Gly Gly
            340                 345

<210> SEQ ID NO 2
<211> LENGTH: 345
<212> TYPE: PRT
<213> ORGANISM: Murinae gen. sp.

<400> SEQUENCE: 2

Met Leu Leu Leu Gly Leu Leu Leu Thr Ser Ala Leu Ala Gly Gln
1               5                   10                  15

Arg Thr Gly Thr Arg Ala Glu Ser Asn Leu Ser Ser Lys Leu Gln Leu
                20                  25                  30

Ser Ser Asp Lys Glu Gln Asn Gly Val Gln Asp Pro Arg His Glu Arg
            35                  40                  45

Val Val Thr Ile Ser Gly Asn Gly Ser Ile His Ser Pro Lys Phe Pro
        50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
            115                 120                 125
```

-continued

```
Val Pro Gly Lys Gln Thr Ser Lys Gly Asn His Ile Arg Ile Arg Phe
    130                 135                 140
Val Ser Asp Glu Tyr Phe Pro Ser Glu Pro Gly Phe Cys Ile His Tyr
145                 150                 155                 160
Ser Ile Ile Met Pro Gln Val Thr Glu Thr Thr Ser Pro Ser Val Leu
                165                 170                 175
Pro Pro Ser Ser Leu Ser Leu Asp Leu Leu Asn Asn Ala Val Thr Ala
            180                 185                 190
Phe Ser Thr Leu Glu Glu Leu Ile Arg Tyr Leu Glu Pro Asp Arg Trp
        195                 200                 205
Gln Val Asp Leu Asp Ser Leu Tyr Lys Pro Thr Trp Gln Leu Leu Gly
    210                 215                 220
Lys Ala Phe Leu Tyr Gly Lys Lys Ser Lys Val Val Asn Leu Asn Leu
225                 230                 235                 240
Leu Lys Glu Glu Val Lys Leu Tyr Ser Cys Thr Pro Arg Asn Phe Ser
                245                 250                 255
Val Ser Ile Arg Glu Glu Leu Lys Arg Thr Asp Thr Ile Phe Trp Pro
            260                 265                 270
Gly Cys Leu Leu Val Lys Arg Cys Gly Asn Cys Ala Cys Cys Leu
        275                 280                 285
His Asn Cys Asn Glu Cys Gln Cys Val Pro Arg Lys Val Thr Lys Lys
    290                 295                 300
Tyr His Glu Val Leu Gln Leu Arg Pro Lys Thr Gly Val Lys Gly Leu
305                 310                 315                 320
His Lys Ser Leu Thr Asp Val Ala Leu Glu His His Glu Glu Cys Asp
                325                 330                 335
Cys Val Cys Arg Gly Asn Ala Gly Gly
            340                 345
```

<210> SEQ ID NO 3
<211> LENGTH: 28
<212> TYPE: DNA
<213> ORGANISM: Murinae gen. sp.

<400> SEQUENCE: 3
cggaattctc agccaaatgc tcctcctc                                         28

<210> SEQ ID NO 4
<211> LENGTH: 59
<212> TYPE: DNA
<213> ORGANISM: Murinae gen. sp.
<220> FEATURE:
<221> NAME/KEY: unsure
<222> LOCATION: (1)..(59)
<223> OTHER INFORMATION: Also contains sequence encoding the human c-myc
      epitope

<400> SEQUENCE: 4
cggatttctt acaagtcttc ttcagaaata agcttttgtt ccccctcctgc gtttcctct    59

<210> SEQ ID NO 5
<211> LENGTH: 18
<212> TYPE: DNA
<213> ORGANISM: Murinae gen. sp.

<400> SEQUENCE: 5
gtgtccatac gggaagag                                                   18

<210> SEQ ID NO 6

-continued

```
<211> LENGTH: 19
<212> TYPE: DNA
<213> ORGANISM: Murinae gen. sp.

<400> SEQUENCE: 6
gtcttcttca gaaataagc                                                19

<210> SEQ ID NO 7
<211> LENGTH: 22
<212> TYPE: PRT
<213> ORGANISM: Murinae gen. sp.
<220> FEATURE:
<221> NAME/KEY: unsure
<222> LOCATION: (1)..(22)
<223> OTHER INFORMATION: Residues 230-250 of mouse PDGF-C (SEQ ID NO:2)

<400> SEQUENCE: 7

Cys Val Lys Lys Ser Arg Val Val Asn Leu Asn Leu Leu Lys Glu Glu
1               5                   10                  15

Val Lys Leu Tyr Ser Cys
            20
```